(12) United States Patent
Toyoda et al.

(10) Patent No.: US 6,639,053 B1
(45) Date of Patent: Oct. 28, 2003

(54) HCV-DERIVED RNA POLYMERASE GENE

(75) Inventors: Tetsuya Toyoda, 1339-4, Tsubukuhonmachi, Kurume-shi, Fukuoka 830-0047 (JP); Michinori Kohara, Chiba (JP); Kyoko Kohara, Chiba (JP); Kazuhiro Higashi, Hyogo (JP); Masayuki Tsuchiya, Shizuoka (JP)

(73) Assignees: Tetsuya Toyoda, Fukuoka (JP); International Reagents Corporation, Hyogo (JP); Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/720,095

(22) PCT Filed: Jun. 24, 1999

(86) PCT No.: PCT/JP99/03381
§ 371 (c)(1),
(2), (4) Date: Dec. 21, 2001

(87) PCT Pub. No.: WO99/67396
PCT Pub. Date: Dec. 29, 1999

(30) Foreign Application Priority Data

Jun. 24, 1998 (JP) .......................................... 10-177817

(51) Int. Cl.[7] .............................................. C07K 14/18
(52) U.S. Cl. ........................ 530/350; 435/5; 435/69.1; 536/23.1; 536/23.2; 536/23.4; 536/23.72
(58) Field of Search .................. 435/5, 69.1; 536/23.1, 536/23.2, 23.4, 23.72; 530/350

(56) References Cited

FOREIGN PATENT DOCUMENTS

| JP | 6-225770 | 8/1994 |
| JP | 10-507370 | 7/1998 |
| JP | 11-514862 | 12/1999 |
| WO | WO 96/37619 | * 11/1996 |

OTHER PUBLICATIONS

Sequence comparison sheet with SEQID No:2 of WO 96/37619.*

Behrens, et al.; "Identification and properties of the RNA–dependent RNA polymerase of hepatitis C virus" The Embo Journal; vol. 15, No. 1, 1996; pp. 12–22.

Hwang, et al.; "Hepatitis C virus NS5B protein is a membrane–associated phosphoprotein with a predominantly perinuclear localization" Virology; vol. 227, No. 2, 1997; pp. 439–446.

Al, R.H. et al., "Expression of Recombinant Hepatitis C Virus Non–Structural Protein 5B in *Escherichia coli*", Virus Research, vol. 53, pp. 141–149, (1998).

Yuan, Z–H. et al., "Expression, Purification, and Partial Characterization of HCV RNA Polymerase", Biochemical and Biophysical Research Communications, vol. 232, No. 1, pp. 231–235, Article No. RC976249, (1997).

Lohmann, V. et al., "Biochemical Properties of Hepatitis C Virus NS5B RNA–Dependent RNA Polymerase and Identification of Amino Acid Sequence Motifs Essential for Enzymatic Activity", Journal of Virology, vol. 71, No. 11, pp. 8416–8428, (1997).

* cited by examiner

*Primary Examiner*—James Housel
*Assistant Examiner*—Myron G. Hill
(74) *Attorney, Agent, or Firm*—Davidson, Davidson & Kappel

(57) ABSTRACT

The present invention provides a gene encoding an RNA polymerase which plays an important role in the reproduction of hepatitis C virus, and a method of screening using this gene or this RNA polymerase protein, thereby allowing easy performance of screening for substances which inhibit the RNA polymerase playing an important role in HCV reproduction.

6 Claims, No Drawings

SEQUENCE LISTING

<160> NUMBER OF SEQ ID NOS: 4

<210> SEQ ID NO 1
<211> LENGTH: 1773
<212> TYPE: DNA
<213> ORGANISM: HCV
<220> FEATURE:

```
<221> NAME/KEY: CDS
<222> LOCATION: (1)...(1773)

<400> SEQUENCE: 1 tca atg tcc tac aca tgg aca ggc gcc ttg atc acg cca tgc gcc gcg       48
Ser Met Ser tyr Thr trp Thr Gly Ala Leu Ile Thr Pro Cys Ala Ala
 1               5                  10                  15 gag gaa agc aag ttg ccc atc aac ccg ttg agc aac tct ttg ttg cgt       96
Glu Glu Ser Lys Leu Pro Ile Asn Pro Leu Ser Asn Ser Leu Leu Arg
             20                  25                  30 cac cac aac atg gtc tat gct aca aca tcc cgc agc gca ggc cta cgg      144
His His Asn Met Val tyr Ala Thr Thr Ser Arg Ser Ala Gly Leu Arg
         35                  40                  45 cag aag aag gtc acc ttt gac aga ctg caa gtc ctg gac gac cac tac      192
Gln Lys Lys Val Thr Phe Asp Arg Leu Gln Val Leu Asp Asp His tyr
     50                  55                  60 cgg gac gtg ctc aag gag atg aag gcg aag gcg tcc aca gtt aag gct      240
Arg Asp Val Leu Lys Glu Met Lys Ala Lys Ala Ser Thr Val Lys Ala
 65                  70                  75                  80 aaa ctc cta tcc ata gaa gaa gcc tgt aag ctg acg ccc cca cat tcg      288
Lys Leu Leu Ser Ile Glu Glu Ala Cys Lys Leu Thr Pro Pro His Ser
                 85                  90                  95 gcc aga tcc aaa ttt ggc tat ggg gca aag gac gtc cgg aac cta tcc      336
Ala Arg Ser Lys Phe Gly tyr Gly Ala Lys Asp Val Arg Asn Leu Ser
            100                 105                 110 agc aag gcc gtt aac cac atc cgc tcc gtg tgg aag gac ttg ctg gaa      384
Ser Lys Ala Val Asn His Ile Arg Ser Val trp Lys Asp Leu Leu Glu
        115                 120                 125 gac act gag aca cca att gac acc acc gtc atg gca aaa agt gag gtt      432
Asp Thr Glu Thr Pro Ile Asp Thr Thr Val Met Ala Lys Ser Glu Val
    130                 135                 140 ttc tgc gtc caa cca gag aaa gga ggc cgc aag cca gct cgc ctt atc      480
Phe Cys Val Gln Pro Glu Lys Gly Gly Arg Lys Pro Ala Arg Leu Ile
145                 150                 155                 160 gta ttc cca gac ttg ggg gtt cgt gta tgc gag aag atg gcc ctt tat      528
Val Phe Pro Asp Leu Gly Val Arg Val Cys Glu Lys Met Ala Leu tyr
                165                 170                 175 gac gtg gtc tcc acc ctt cct cag gcc gtg atg ggc tcc tca tac gga      576
Asp Val Val Ser Thr Leu Pro Gln Ala Val Met Gly Ser Ser tyr Gly
            180                 185                 190 ttc cag tac tcc cct gga cag cgg gtc gag ttc ctg gtg aat gcc tgg      624
Phe Gln tyr Ser Pro Gly Gln Arg Val Glu Phe Leu Val Asn Ala trp
        195                 200                 205 aaa tca aag aaa tgc cct atg ggc ttt tca tat gac acc cgc tgt ttt      672
Lys Ser Lys Lys Cys Pro Met Gly Phe Ser tyr Asp Thr Arg Cys Phe
    210                 215                 220 gac tcg aca gtc act gag agt gac atc cgt gtt gag gag tca att tac      720
Asp Ser Thr Val Thr Glu Ser Asp Ile Arg Val Glu Glu Ser Ile tyr
225                 230                 235                 240 caa tgt tgt gac ttg gcc ccc gaa gcc aga cag gcc ata aag tcg ctc      768
Gln Cys Cys Asp Leu Ala Pro Glu Ala Arg Gln Ala Ile Lys Ser Leu
                245                 250                 255 aca gag cgg ctt tac att ggg ggt ccc ctg acc aat tca aaa ggg cag      816
Thr Glu Arg Leu tyr Ile Gly Gly Pro Leu Thr Asn Ser Lys Gly Gln
            260                 265                 270 aac tgt ggc tat cgc cgg tgc cgc gcg agt ggc gtg ctg acg acc agc      864
Asn Cys Gly tyr Arg Arg Cys Arg Ala Ser Gly Val Leu Thr Thr Ser
        275                 280                 285 tgc ggt aat acc ctt aca tgt tac ttg aag gcc tct gca gcc tgt cga      912
Cys Gly Asn Thr Leu Thr Cys tyr Leu Lys Ala Ser Ala Ala Cys Arg
```

```
                      290                    295                   300
gct gca aag ctc cgg gac tgc acg atg ctc gtg aac gga gac gac ctc       960
Ala Ala Lys Leu Arg Asp Cys Thr Met Leu Val Asn Gly Asp Asp Leu
305                 310                 315                 320 gtc gtc atc tgt gag agt gcg gga acc caa gag gat gag gcg aac cta      1008
Val Val Ile Cys Glu Ser Ala Gly Thr Gln Glu Asp Glu Ala Asn Leu
                325                 330                 335 cga gtc ttc acg gag gct atg act agg tat tct gcc ccc ccc ggg gac      1056
Arg Val Phe Thr Glu Ala Met Thr Arg tyr Ser Ala Pro Pro Gly Asp
            340                 345                 350 ccg ccc cga cca gaa tac gac ttg gag cta ata aca tca tgt tcc tcc      1104
Pro Pro Arg Pro Glu tyr Asp Leu Glu Leu Ile Thr Ser Cys Ser Ser
        355                 360                 365 aat gtg tcg gtc gcg cac gat gca tct ggc aaa agg gta tac tac ctc      1152
Asn Val Ser Val Ala His Asp Ala Ser Gly Lys Arg Val tyr tyr Leu
    370                 375                 380 acc cgc gac ccc tcc acc ccc ctt gca cgg gct gcg tgg gag aca gct      1200
Thr Arg Asp Pro Ser Thr Pro Leu Ala Arg Ala Ala trp Glu Thr Ala
385                 390                 395                 400 aga cac act cca gtt aat tcc tgg cta ggc aac atc att atg tat gcg      1248
Arg His Thr Pro Val Asn Ser trp Leu Gly Asn Ile Ile Met tyr Ala
                405                 410                 415 ccc acc tta tgg gca agg atg att ctg atg acc cat ttc ttc tcc atc      1296
Pro Thr Leu trp Ala Arg Met Ile Leu Met Thr His Phe Phe Ser Ile
            420                 425                 430 ctt cta gcc cag gag caa ctt gaa aaa gcc ctg gat tgc cag atc tac      1344
Leu Leu Ala Gln Glu Gln Leu Glu Lys Ala Leu Asp Cys Gln Ile tyr
        435                 440                 445 ggg gcc tgt tac tcc att gag cca ctt gac cta cct cag atc att gaa      1392
Gly Ala Cys tyr Ser Ile Glu Pro Leu Asp Leu Pro Gln Ile Ile Glu
    450                 455                 460 cga ctc cat ggt ctt agc gca ttt tca ctc cat agt tac tct cca ggt      1440
Arg Leu His Gly Leu Ser Ala Phe Ser Leu His Ser tyr Ser Pro Gly
465                 470                 475                 480 gag atc aat agg gtg gct tca tgc ctc agg aaa ctt ggg gta cca ccc      1488
Glu Ile Asn Arg Val Ala Ser Cys Leu Arg Lys Leu Gly Val Pro Pro
                485                 490                 495 ttg cga gtc tgg aga cat cgg gcc aga agt gtc cgc gct aag ctg ctg      1536
Leu Arg Val trp Arg His Arg Ala Arg Ser Val Arg Ala Lys Leu Leu
            500                 505                 510 tcc cag ggg ggg agg gct gcc act tgt ggt aag tac ctc ttc aac tgg      1584
Ser Gln Gly Gly Arg Ala Ala Thr Cys Gly Lys tyr Leu Phe Asn trp
        515                 520                 525 gca gta agg acc aag ctc aaa ctc act cca atc ccg gca gcg tcc cag      1632
Ala Val Arg Thr Lys Leu Lys Leu Thr Pro Ile Pro Ala Ala Ser Gln
    530                 535                 540 ttg gac ttg tcc agc tgg ttc gtg gct ggt tac agc ggg gga gac ata      1680
Leu Asp Leu Ser Ser trp Phe Val Ala Gly tyr Ser Gly Gly Asp Ile
545                 550                 555                 560 tat cac agc ctg tct cgt gcc cga ccc cgc tgg ttc atg ttg tgc cta      1728
tyr His Ser Leu Ser Arg Ala Arg Pro Arg trp Phe Met Leu Cys Leu
                565                 570                 575 ctc cta ctt tca gta ggg gta ggc atc tac ctg ctc ccc aac cga          1773
Leu Leu Leu Ser Val Gly Val Gly Ile tyr Leu Leu Pro Asn Arg
            580                 585                 590

<210> SEQ ID NO 2
<211> LENGTH: 591
<212> TYPE: PRT
<213> ORGANISM: HCV
```

-continued

```
<400> SEQUENCE: 2

Ser Met Ser tyr Thr trp Thr Gly Ala Leu Ile Thr Pro Cys Ala Ala
 1               5                  10                  15

Glu Glu Ser Lys Leu Pro Ile Asn Pro Leu Ser Asn Ser Leu Leu Arg
            20                  25                  30

His His Asn Met Val tyr Ala Thr Thr Ser Arg Ser Ala Gly Leu Arg
         35                  40                  45

Gln Lys Lys Val Thr Phe Asp Arg Leu Gln Val Leu Asp Asp His tyr
     50                  55                  60

Arg Asp Val Leu Lys Glu Met Lys Ala Lys Ala Ser Thr Val Lys Ala
 65                  70                  75                  80

Lys Leu Leu Ser Ile Glu Glu Ala Cys Lys Leu Thr Pro Pro His Ser
                 85                  90                  95

Ala Arg Ser Lys Phe Gly tyr Gly Ala Lys Asp Val Arg Asn Leu Ser
            100                 105                 110

Ser Lys Ala Val Asn His Ile Arg Ser Val trp Lys Asp Leu Leu Glu
        115                 120                 125

Asp Thr Glu Thr Pro Ile Asp Thr Thr Val Met Ala Lys Ser Glu Val
    130                 135                 140

Phe Cys Val Gln Pro Glu Lys Gly Gly Arg Lys Pro Ala Arg Leu Ile
145                 150                 155                 160

Val Phe Pro Asp Leu Gly Val Arg Val Cys Glu Lys Met Ala Leu tyr
                165                 170                 175

Asp Val Val Ser Thr Leu Pro Gln Ala Val Met Gly Ser Ser tyr Gly
            180                 185                 190

Phe Gln tyr Ser Pro Gly Gln Arg Val Glu Phe Leu Val Asn Ala trp
        195                 200                 205

Lys Ser Lys Lys Cys Pro Met Gly Phe Ser tyr Asp Thr Arg Cys Phe
    210                 215                 220

Asp Ser Thr Val Thr Glu Ser Asp Ile Arg Val Glu Glu Ser Ile tyr
225                 230                 235                 240

Gln Cys Cys Asp Leu Ala Pro Glu Ala Arg Gln Ala Ile Lys Ser Leu
                245                 250                 255

Thr Glu Arg Leu tyr Ile Gly Gly Pro Leu Thr Asn Ser Lys Gly Gln
            260                 265                 270

Asn Cys Gly tyr Arg Arg Cys Arg Ala Ser Gly Val Leu Thr Thr Ser
        275                 280                 285

Cys Gly Asn Thr Leu Thr Cys tyr Leu Lys Ala Ser Ala Ala Cys Arg
    290                 295                 300

Ala Ala Lys Leu Arg Asp Cys Thr Met Leu Val Asn Gly Asp Asp Leu
305                 310                 315                 320

Val Val Ile Cys Glu Ser Ala Gly Thr Gln Glu Asp Glu Ala Asn Leu
                325                 330                 335

Arg Val Phe Thr Glu Ala Met Thr Arg tyr Ser Ala Pro Pro Gly Asp
            340                 345                 350

Pro Pro Arg Pro Glu tyr Asp Leu Glu Leu Ile Thr Ser Cys Ser Ser
        355                 360                 365

Asn Val Ser Val Ala His Asp Ala Ser Gly Lys Arg Val tyr tyr Leu
    370                 375                 380

Thr Arg Asp Pro Ser Thr Pro Leu Ala Arg Ala Ala trp Glu Thr Ala
385                 390                 395                 400

Arg His Thr Pro Val Asn Ser trp Leu Gly Asn Ile Ile Met tyr Ala
```

-continued

```
                          405                 410                 415
Pro Thr Leu trp Ala Arg Met Ile Leu Met Thr His Phe Phe Ser Ile
            420                 425                 430

Leu Leu Ala Gln Glu Gln Leu Glu Lys Ala Leu Asp Cys Gln Ile tyr
            435                 440                 445

Gly Ala Cys tyr Ser Ile Glu Pro Leu Asp Leu Pro Gln Ile Ile Glu
            450                 455                 460

Arg Leu His Gly Leu Ser Ala Phe Ser Leu His Ser tyr Ser Pro Gly
465                 470                 475                 480

Glu Ile Asn Arg Val Ala Ser Cys Leu Arg Lys Leu Gly Val Pro Pro
            485                 490                 495

Leu Arg Val trp Arg His Arg Ala Arg Ser Val Arg Ala Lys Leu Leu
            500                 505                 510

Ser Gln Gly Gly Arg Ala Ala Thr Cys Gly Lys tyr Leu Phe Asn trp
            515                 520                 525

Ala Val Arg Thr Lys Leu Lys Leu Thr Pro Ile Pro Ala Ala Ser Gln
            530                 535                 540

Leu Asp Leu Ser Ser trp Phe Val Ala Gly tyr Ser Gly Gly Asp Ile
545                 550                 555                 560 tyr His Ser Leu Ser Arg Ala Arg Pro Arg trp Phe Met Leu Cys Leu
                565                 570                 575

Leu Leu Leu Ser Val Gly Val Gly Ile tyr Leu Leu Pro Asn Arg
            580                 585                 590

<210> SEQ ID NO 3
<211> LENGTH: 30
<212> TYPE: DNA
<213> ORGANISM: Artificial Sequence
<220> FEATURE:
<223> OTHER INFORMATION: Primer

<400> SEQUENCE: 3
atccctcgag atgtcctaca catggacagg                                    30

<210> SEQ ID NO 4
<211> LENGTH: 34
<212> TYPE: DNA
<213> ORGANISM: Artificial Sequence
<220> FEATURE:
<223> OTHER INFORMATION: Primer

<400> SEQUENCE: 4
tatggatcca agcttcaccg gttggggagc aggt                               34
```

HCV-DERIVED RNA POLYMERASE GENE

This application is a 371 of PCT/JP99/03381, filed Jun. 24, 1999.

TECHNICAL FIELD

The present invention relates to an RNA polymerase gene derived from hepatitis C virus (referred to as "HCV" herein), a method of screening using this gene or this RNA polymerase protein, and a substance able to be isolated by this screening method.

PRIOR ART

Generally known viral hepatitis includes hepatitis A which is mainly orally transmitted, and hepatitis B transmitted by means of the blood. Moreover, apart from these hepatitis, there is hepatitis called non-A, non-B hepatitis which is transmitted by means of blood transfusion. Since most of these infected with non-A, non-B hepatitis become chronic, and the incidence of development into cirrhosis and hepatoma is high, this is one disease for which the establishment of a certain means of treatment is urgently sought.

Through the causative agent of non-A, non-B hepatitis had been unclear for a long time, recently the causative virus was isolated by M. Houghton et al. (Japanese Patent Application Laid-Open (Kohyo) No. 2-500880), and was termed "HCV". HCV is a single-stranded RNA virus belonging to the Flaviviridae, the length of its whole genomic RNA is about 9.4 kb. The genomic RNA is divided into 7 regions; core, E1, E2/NS1, NS2, NS3, NS4, and NS5; and the genes related to virus growth, etc. are primarily included in downstream regions from NS3.

HCV RNA polymerase is related to the transcription and replication of genomic RNA, and plays an important role in the reproduction of HCV. The gene encoding this polymerase is thought to be included in the above-mentioned NS5 region (Z. H. Yuan et al., Biochemical and Biophysical Research Communications 232, 231–235(1997), S. B. Hwang et al., Virology 227, 439–446(1997), S. E. Behrens et al., The EMBO Journal 15 12–22(1996)).

The Problem to Be Solved by the Invention

If the gene encoding HCV RNA polymerase can be isolated, it will become possible using this gene to easily screen for substances inhibiting RNA polymerase, and contribute greatly to the development of drugs for treating HCV. However, at present, although the nucleotide sequence of a portion of the NS5 region has been clarified (Japanese Patent Application Laid-Open (Kokai) No. 6-225770), the entire nucleotide sequence of the RNA polymerase gene has yet to be clarified.

The object of the present invention is to isolate the gene encoding the full length of HCV-derived RNA polymerase, to determine its nucleotide sequence, as well as to establish its expression system.

A further object of the present invention is to provide a screening method for a substance which inhibits the activity of this gene or this protein employing this gene or this RNA polymerase protein.

Means for Solving the Problem

In order to solve the above problem, the present inventors, as result of deliberate and focused research have succeeded in isolating the gene encoding the full-length of HCV-derived RNA polymerase, thereby completing the present invention.

That is to say, the present invention relates to the following (1) to (3).

(1) A gene encoding the following protein (a) or (b):
  (a) a protein consisting of the amino acid sequence represented in SEQ ID NO:2;
  (b) a protein consisting of an amino acid sequence derived from the amino acid sequence represented in SEQ ID NO:2 by deletion, substitution or addition of one or several amino acid(s), and which has RNA polymerase activity.

(2) A method of screening a substance which inhibits the activity of the gene of (1) above, or of the protein consisting of the amino acid sequence represented in SEQ ID NO: 2, wherein this method comprises the following steps:
  (a) a step of contacting the gene of (1) above or the protein consisting of the amino acid sequence represented in SEQ ID NO: 2, or a fragment of this protein, with a test sample; and,
  (b) a step of selecting a substance which inhibits the activity of the gene of (1) above, or of the protein or the partial peptide fraction consisting of the amino acid sequence represented in SEQ ID NO: 2.

(3) A substance able to be isolated by the method of (2) above, wherein this substance inhibits the activity of the gene of (1) above or of the protein consisting of the amino acid sequence represented in SEQ ID NO: 2.

The descriptions contained in the specification of Japanese Patent Application No. 10-177817, which forms the basis of the right of priority of the present application, are incorporated herein in their entirety.

DISCLOSURE OF THE INVENTION

Below, the present invention will be explained in detail.

The gene of the present invention encodes (a) a protein consisting of the amino acid sequence represented in SEQ ID NO: 2; or, (b) a protein consisting of an amino acid sequence derived from the amino acid sequence represented in SEQ ID NO:2 by deletion, substitution, or addition of one or several amino acid(s) and having RNA polymerase activity.

The deletion, etc. of one or several amino acid can be performed by techniques in common use at the time of filing this application, such as, for example, site-specific mutagenesis (Nucleic Acids Res. 10, 6487–6500, 1982).

The gene of the present invention is able to be obtained from the blood of non-A, non-B hepatitis patients as described in the examples, or from the strain of E. coli into which a vector (pCALN/HCV RBZ) comprising the gene of the present invention was introduced, has been deposited at the National Institute of Bioscience and Human-Technology, Agency of Industrial Science and Technology (1-1-3, Higashi, Tsukuba-shi, Ibaraki-ken, Japan) (Accession No. FERM BP-6763) on Oct. 31, 1997).

Further, the present invention relates to a screening method for a substance which inhibits the activity of this gene or this protein, employing the gene of the present invention or an RNA polymerase protein consisting of the amino acid sequence represented in SEQ ID NO: 2; and, to a substance able to be isolated by this screening method employing this gene or this RNA polymerase protein.

The RNA polymerase encoded by the gene of the present invention is an enzyme involved in the transcription and replication of HCV genomic RNA. Therefore, a substance which inhibits this enzyme is thought to be able to prevent the reproduction of HCV, and is promising as a drug for treating non-A, non-B hepatitis. By using the gene of the present invention it will be possible to produce HCV-derived RNA polymerase easily and in great quantities, and as a result of this, the screening of inhibitory substances for the RNA polymerase will become simpler.

The protein of the present invention that can be used for screening can be either a recombinant type, a wild type, or a partial peptide. Further it can be a purified peptide or a partial peptide thereof.

One embodiment of this method of screening comprises the steps of (a) contacting the gene of the present invention or the protein consisting of the amino acid sequence represented by SEQ ID NO: 2, or a fragment of this protein, with a test sample; and, (b) selected a substance which inhibits the activity of the gene of the present invention or the protein consisting of the amino acid sequence represented by SEQ ID NO: 2. There is no particular limitation on what can be used as a test material in this screening method but for example, a cell extract, a cell culture supernatant, a protein, a peptide, or synthetic low molecular weight compound can be used.

EXAMPLES (1) Isolation of HCV RNA from the Blood of a Hepatitis Patient and PCR Amplification of the Isolated RNA RNA was extracted from the blood of a non-A, non-B hepatitis patient by guanidine thiocyanate and phenol/chloroform method and RT-PCR was performed according to the method described in Japanese Patent Application Laid-Open (Kokai) No. 6-225770. Using this cDNA as a template, PCR (Science 230:1350(1985)) was performed using the primers described in Japanese Patent Application Laid-Open (Kokai) No. 6-225770, and four types of amplification fragment (C6-62 region, C6-66 region, C6-79 region, C6-82 region) were obtained. These amplification fragments were cloned using cloning vector pBM, and the nucleotide sequences of the amplification fragments were determined by Sanger's dideoxy- termination procedure (Science, 214, 1205(1981)). It should be noted that cloning vector pBM is a vector that was constructed such that mutations do not occur easily, taking into consideration the nature of the HCV gene to incorporate mutations easily during replication and cloning. (Japanese Patent Application Laid-Open (Kokai) No. 6-225770).

The position of each amplification fragment was determined by a comparison of the homology of the amplification fragments within the clones obtained by the above method, and the previously reported non-A, non-B hepatitis virus gene, each of these amplification fragments were joined together by PCR, and the desired DNA fragment (amplified DNA) was cloned into a vector. pCALN/HCV RBZ was prepared using this cloning vector.

(2) Determining the Nucleotide Sequence of the Fragment Encoding NS5B

The fragment encoding NS5B was amplified by PCR with pCALN/HCV RBZ as a template using the following primers.

PCR primers:

NS5B1 5'-ATC CCT CGA GAT GTC CTA CAC ATG GAC AGG-3' (SEQ ID NO:3)

NS5B2 5'-TAT GGA TCC AAG CTT CAC CGG TTG GGG AGC AGG T-3' (SEQ ID NO:4)

The reaction solution was prepared by adding to a 0.5 ml tube, 10 µl 10×PCR buffer II (500 mM KCl , 100 mM Tris-HCl pH8.3, 15 mM MgCl$_2$), 16 µl of 1.25 mM dNTP, 5 µl each of the 2 types of primers (20 µM) (NS5B1, NS5B2), 0.5 µl of 1 units/µl AmpliTaq DNA Polymerase (PERKIN ELMER) and adjusting to 100 µl with sterilized water. Thermal conditions were set such that, after initial heating at 95° C. for 5 minutes, 25 cycles were conducted with conditions of 95° C. for 1 minute for denaturation, 55° C. for 1 minute for annealing, and 72° C. for 3 minutes for extension, and thereafter was finally maintained at 72° C. for 10 minutes. A portion of the post-reaction solution was subjected to agarose gel electrophoresis, and the specifically amplified DNA fragment was confirmed.

After purifying this DNA fragment according to the Gene Clean (Biolol) method, the fragment was digested with XhoI and BamHI. The digested reaction solution was subjected to agarose gel electrophoresis, the desired DNA fragment was extracted from the gel, and the concentration of DNA in the extract was measured. The cloning vector pET-15b (Novagen) was similarly digested with XhoI and BamH, then purified. The digested reaction solution was subjected to agarose gel electrophoresis, the desired DNA fragment was extracted from the gel and the concentration of DNA in the extract was measured.

In respect the above-mentioned two types of DNA fragment extracted from the gel, a ligation reaction was performed according to the DNA ligation Kit ver.2 (Takara) method, and E. coli was transformed using a portion of the reaction solution. The transformed strain thereby obtained was cultured overnight on an LB-Amp plate(1% bactotryptone, 0.5% yeast extract, 1% NaCl, 1.4% agar, ampicillin 100 µg/ml). Thereafter, the colonies appearing on the plate were each cultured (37° C., 16 hours) with a tube containing 2 ml LB-Amp medium(1% bactotryptone, 0.5%yeast extract, 1% NaCl, ampicillin 100 µg/ml). The cultured fluid was centrifuged to collect the microorganism and plasmid DNA was extracted by mini-preparation method. The plasmid was digested with XhoI and BamHI, and then the digested product was subjected to agarose gel electrophoresis, and a plasmid clone into which the desired DNA fragment had been introduced, was obtained. This plasmid clone was designated pET-15b HCV pol.

The plasmid clone pET-15b HCV pol obtained above was digested with XbaI and BamHI, this product solution of the enzyme reaction was subjected to agarose gel electrophoresis and the desired DNA fragment was extracted. Similarly, baculovirus transfer vector pVL1392 (Pharmigen) was digested with XbaI and BamHI, this product solution of the enzyme reaction was subjected to agarose gel electrophoresis, and the desired DNA fragment was extracted.

By performing a ligation reaction with respect to the above-mentioned two types of DNA fragment extracted from agarose-gel, NS5B gene tagged with 6×His at the N-terminus was introduced into pVL1392. E. coli was transformed using this ligation reaction solution. The obtained transformed strain was cultured overnight on LB-Amp plate (1% bactotryptone, 0.5% yeast extract, 1% NaCl, 1.4% agar, ampicillin 100 µg/ml), thereafter each colony appearing on the plate was cultured (37° C., 16 hours) with a tube containing 2 ml LB-Amp medium (1%bactotryptone, 0.5% yeast extract, 1% NaCl, ampicillin 100 µg/ml). After the cultured fluid was centrifuged, the plasmid DNA was miniprepped and DNA solution was prepared. After digested with XbaI and BamHI, the product solution of the enzyme reaction was subjected to agarose gel electrophoresis, and a clone into which the desired DNA fragment had been introduced was obtained. This clone was designated pVL1392 His HCV pol. Using pVL1392 His HCV pol, a recombinant baculovirus (BacHisHCVpol) was produced with BaculoGold (Pharmigen). Production of the baculovirus was performed in accordance with the descriptions in "Baculovirus Expression Vector System: Procedures and Methods Manual" (Pharmigen).

(3) Expression and Purification of RNA Polymerase sf21 AE cells were infected with BacHisHCVpol, with moi=1 or 2, and three days after infection (72 hours later), cells were collected, and extracted with a buffer comprising 10 mM Tris/HCl pH7.9, 0.5M NaCl, 1.5 mM MgCl$_2$, 7 mM 2-ME, 0.1% Triton X-100, 25% glycerol, 1 mM PMSF, and 10 µg/ml leupeptin. The whole cell extract was first passed through a Ni-NTA column (QIAGEN, 60 mM imidazole), then purified with FPLC (MonoQcolumn, Pharmacia). RNA polymerase was eluted from MonoQ column with a buffer containing 0.1–1.0 M NaCl gradient.

(4) Confirmation of RNA Polymerase Activity

Preceding measurement of HCV RNA polymerase activity, in order to determine the optimal concentrations for magnesium acetate and KCl reactions, an RNA specific to HCV was produced as an RNA polymerase reaction template.

HCV cDNA downstream of the PvuII site (9240) of HCV was cloned into Bluescript KSII (+), this vector was designated HCV RNA-9610. The prepared cloning vector Bluescript KSII (+) HCV RNA-9610 was digested with DraI, PstI, NheI, etc. and after purification, was supplied to an in vitro transcription reaction using T7 RNA polymerase. Due to the differences in the restriction enzymes that were used; DraI, PstI and NheI; the synthesized RNA differed in length (377 nts in the case of DraI, 340 nts in the case of PstI, and 305 nts in the case of NheI). These RNA were designated HCV RNA-9610, HCV RNA-9576, HCV RNA-9541, respectively. It should be noted that HCV RNA-9610 has two extra UMPs at its 3' terminus.

With the above-mentioned HCV RNA as a template, the optimal concentration of magnesium acetate in the HCV RNA polymerase activity measurement system was determined. HCV RNA polymerase (MonoQ column fraction) 5 µl was added to 50 µl of buffer (20 mM HEPES/KOH pH7.6, 50 mM KCl, 1 mM DTT, 25 µg/ml actinomycin D, 0.5 mM ATP,CTP,GTP, 50 µM UTP, 5µ Ci[α-$^{32}$P] UTP (15 TBq/mmol, Amersham), 10 pmole HCV RNA-9541, 400 U/ml RNase inhibitor (TOYOBO)), and in this solution, the concentration of magnesium acetate was set at eleven levels within a range of 0–10 mM and incubated at 29° C. for 1.5 hours. Products were synthesized at each magnesium acetate concentration and subjected to electrophoresis with 4% PAGE/6M urea. The PSL of the product was measured with BAS. As a result, optimal magnesium acetate concentration was 3–4 mM.

Similarly, the optimal concentration of KCl in the HCV RNA polymerase activity measurement system was determined. Here polyA was used as a template instead of HCV RNA. 10 µl of HCV RNA polymerase fraction was added to 50 µl of buffer (20 mM HEPES/KOH pH7.6, 5 mM magnesium acetate, 1 mM DTT, 25 µg/ml actinomycin D, 10 µM UTP, 2.5µ Ci[α-$^{32}$P] UTP(15 TBq/mmol, Amersham), 10 µg/ml poly A(Pharmacia), 100 µM UpU(Sigma), 400 U/ml RNase inhibitor (Takara)), and the KCl concentration was set at 10 levels within a range of 20–200 mM, and the amount of UMP uptake at each concentration was measured.

This measurement itself was performed by firstly, by precipitation of the [α-$^{32}$P] UMP that was taken up within 10% TCA, collection on a glass filter(GF/C, Whatman), and measuring with a liquid scintillation counter (Aloka). With polyA as a template, the optimal salt concentration of KCl in the polymerase activity observation system, in the presence of UpU primer, was 100 mM.

Further, the KCl optimal concentration of the HCV RNA polymerase activity measurement system in the case where HCV RNA-9541 is used as a template, was determined. In the reaction system, the amount of HCV RNA polymerase was set at 5 µl, the magnesium acetate concentration was set at 3.5 mM, 10 pmole of HCV RNA-9541 was used as a template but otherwise the reaction system was identical to the experimental system for determining the optimal concentration of magnesium acetate. The concentration of KCl was set at nine levels within a range of 50–200 mM. The result of this measurement was that the optimal concentration of KCl was 50 mM. Here, the cause of the difference in KCl optimal concentration was presumed to be due to the secondary structure of the template.

(5) Inhibition of the Uptake of UMP of HCV RNA Polymerase by Rabbit Anti-HCV RNA Polymerase Antibodies NS5B (HCV RNA polymerase) within pET-15b HCV pol was expressed in *E. coli*, and then purified with a Ni-NTA (QIAGEN) column. A rabbit was immunized using this protein as an antigen, and antibodies were (anti-HCVpol) produced.

First, 20 µl of HCV RNA polymerase purified with Ni-NTA and incubated at room temperature for 30 minutes under the conditions of a final concentration of 3.1, 6.3, 12.5, 25, 50 µg/ml of rabbit IgG anti-HCV RNA polymerase; or as a control, normal rabbit IgG. The composition of the buffer that was used was 20 mM HEPES/KOH pH7.6, 100 mM KCl.

After incubation, this HCV RNA polymerase solution was re-adjusted such that it was composed of 3 mM magnesium acetate, 1 mM DTT, 25 µg/ml actinomycin D, 10 µM UTP (Pharmacia), 2.5µ Ci[α-$^{32}$P] UTP(15 TBq/mmol, Amersham), 10 µg/ml poly A(Pharmacia), 100 µM UpU (Sigma), 400 U/ml Prime RNase inhibitor(5'-3' Inc.), and incubated at 29° C. for 1.5 hours. The [α-$^{32}$P] UMP that was taken up was precipitated in 10% TCA, collected on a glass filter(GF/C, Whatman), and measured with a liquid scintillation counter (Aloka). As a result, inhibition of the uptake of UMP of HCV RNA polymerase by the rabbit anti-HCV RNA polymerase anti-body was observed.

All publications, patents and patent publications cited herein are incorporated into this specification in their entirety.

Effect of the Invention

The present invention provides a novel RNA polymerase gene derived from hepatitis C virus and a method of screening using this gene or this RNA polymerase protein. Screening of an inhibitory substance of this RNA polymerase can be easily performed by using this gene.

What is claimed is:

1. An isolated nucleic acid encoding a protein comprising the amino acid sequence represented in SEQ ID NO:2.

2. An isolated nucleic acid encoding a protein comprising the amino acid sequence in which one amino acid is deleted from or added to the amino acid sequence represented in SEQ ID NO:2, and having RNA polymerase activity.

3. An isolated protein comprising the amino acid sequence represented in SEQ ID NO:2 and having RNA polymerase activity.

4. An isolated protein comprising the amino acid sequence in which one amino acid is deleted from or added to the amino acid sequence represented in SEQ ID NO:2, and having RNA polymerase activity.

5. A method of identifying a substance which inhibits RNA polymerase activity of the protein of claim 3, wherein said method comprises the following steps:

(a) contacting the protein with test substance;

(b) measuring an activity of the protein; and (c) determining if the substance inhibits the activity of the protein.

6. A method of identifying a substance which inhibits RNA polymerase activity of the protein of claim 4, wherein said method comprises the following steps:

(a) contacting the protein with test substance;

(b) measuring an activity of the protein; and (c) determining if the substance inhibits the activity of the protein.

* * * * *